United States Patent [19]

Bondiou et al.

[11] Patent Number: 4,546,185

[45] Date of Patent: Oct. 8, 1985

[54] PROCESS FOR THE PREPARATION OF DERIVATIVES OF QUINUCLIDINE SUBSTITUTED IN THE 3 POSITION

[75] Inventors: Jean-Claude Bondiou, Montrouge; Francoise Hodac, Paris; Didier Legroux, Domont, all of France

[73] Assignee: Pharmuka Laboratoires, Gennevilliers, France

[21] Appl. No.: 522,288

[22] Filed: Aug. 11, 1983

[30] Foreign Application Priority Data

Aug. 17, 1982 [FR] France .................. 82 14215

[51] Int. Cl.$^4$ .................................. C07D 453/02
[52] U.S. Cl. ................................................ 546/133
[58] Field of Search ......................... 546/133

[56] References Cited

PUBLICATIONS

*Chemical Abstracts,* 90:5881f (1979) [Sato, M., et al., Jpn. Kokai 78, 103, 426, 9/8/78].
*Chemical Abstracts,* 97:92548p (1982) [Sato, M., Jpn. Kokai 82, 26, 694, 2/12/82].
Ashby E., et al., *J. Org. Chem.,* 45,1035 (1980).

*Primary Examiner*—Richard A. Schwartz

*Attorney, Agent, or Firm*—Beveridge, DeGrandi and Weilacher

[57] ABSTRACT

Process for the preparation of compounds of the formula:

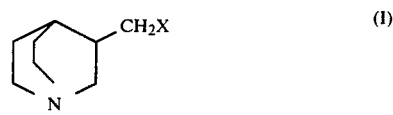

(I)

in which X is H, Cl, Br, I or OH, in which 3-methylene quinuclidine is reacted with an aluminum hydride, in an appropriate solvent and in the presence of a catalytic quantity of a halide of a transition metal, the molar ratio $$\frac{\text{aluminum hydride}}{\text{3-methylene quinuclidine}}$$

being at least equal to 0.6, the product formed is reacted in situ with an ester, and then the product thus formed is reacted in situ with an electrophilic reactant which is capable of yielding an atom or group X as defined with reference to formula (I). The compounds of formula (I) can be used for the preparation of medicaments.

8 Claims, No Drawings

PROCESS FOR THE PREPARATION OF DERIVATIVES OF QUINUCLIDINE SUBSTITUTED IN THE 3 POSITION

The present invention is concerned with a new process for the preparation of derivatives of quinuclidine of the formula:

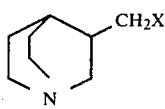 (I)

in which X is a hydrogen, chlorine, bromine or iodine atom or a hydroxyl (OH) group.

The compounds of formula (I) are known products, which can be used, in particular, as intermediate products for the preparation of medicaments (cf. for example, French Pat. Nos. 2,034,605 and 2,052,991). They have been prepared starting from 3-quinuclidinone by C. A. Grob and E. Renk (Helvetica Chemica Acta 1954, Vol. 37, p. 1689–1698) according to a process which involves a minimum of 6 stages, and which can be indicated schematically, as follows:

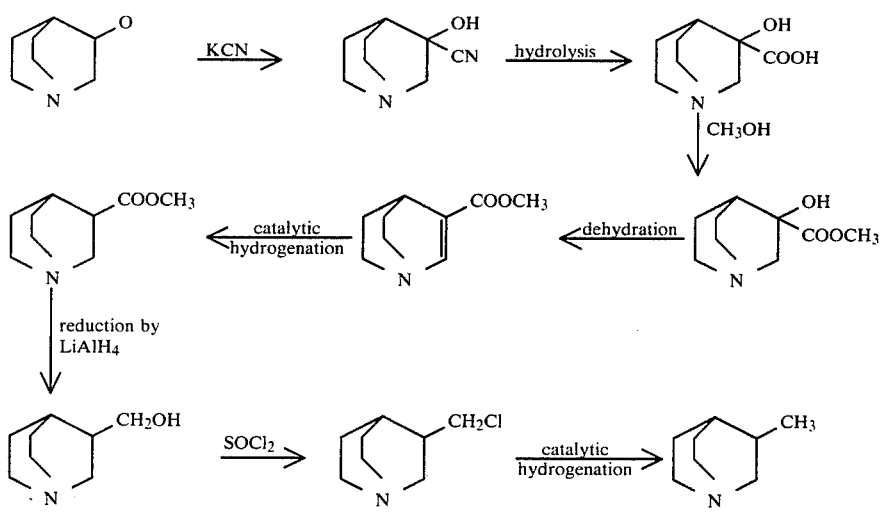

The process according to the invention consists of:

(a) reacting, in an appropriate solvent and in the presence of a catalytic quantity of a halide of a transition metal, 3-methylene quinuclidine of the formula:

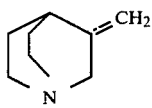 (II)

with an aluminum hydride, at a molar ratio

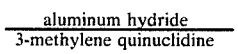

which is at least equal to 0.6;

(b) reacting in situ, the product formed in step (a) with an ester; and (c) reacting in situ, the product formed in step (b) with an electrophilic reactant capable of yielding an atom or group X, X having the significance indicated in formula (I).

Solvents which can be used in step (a) may be, for example, tetrahydrofuran, dimethoxyethane (or dimethyl ether of ethylene glycol), diglyme, triglyme, mixtures of the above compounds, and mixtures of these compounds with an aromatic hydrocarbon such as benzene or toluene containing, at most, 50% by volume of aromatic hydrocarbon. Halides of a transition metal which may be used in step (a) are, in particular, titanium tetrachloride, zirconium tetrachloride, cobalt chloride and nickel chloride. Aluminum hydrides which can be used in step (a) are, in particular, lithium aluminum hydride ($LiAlH_4$) and bis(2-methoxy ethoxy) aluminum hydride. Step (a) is carried out at a temperature between the ambient temperature (15° C. to 25° C.) and the boiling point of the solvent. It is preferably carried out at the ambient temperature.

When in step (a), $LiAlH_4$ is used as the aluminum hydride and $TiCl_4$ is used as the halide of a transition metal, then the reaction is carried out preferably at a molar ratio

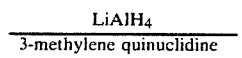

of 1.2 to 1.3 and at a molar ratio

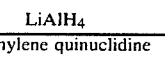

between 10 and 25, and more particularly, about 17. Under these conditions, and operating at ambient temperature in a medium of a toluene-tetrahydrofuran (or dimethoxyethane) mixture containing 3 parts by volume of toluene per 5 parts by volume of tetrahydrofuran (or dimethoxyethane), step (a) is complete after agitating the reaction medium for 24 hours.

Esters which may be used in step (b) are, in particular, the esters of saturated aliphatic alcohols having 1 to 6 carbon atoms with monocarboxylic saturated aliphatic acids having 1 to 6 carbon atoms, and more especially, ethyl acetate and methyl formate. Step (b) is preferably carried out at a temperature between −5° C. and the ambient temperature.

Electrophilic reactants which may be used in step (c) are:

as reactants which can yield an atom of chlorine: chlorine, copper chloride (cupric chloride) or N-chloro succinimide;

as reactants which can yield an atom of bromine: bromine, copper bromide, N-bromo succinimide and dibromohydantoin;

as reactant which can yield an atom of iodine: iodine;

as reactant which can yield an atom of hydrogen: water;

as reactants which can yield a hydroxyl group: hydrogen peroxide and organic hydroperoxides (for example, tert-butyl hydroperoxide).

The temperature conditions used in step (c) are a function of the electrophilic reactant involved. The table below gives the temperature conditions which may be used for some of the electrophilic reactants cited above.

| Electrophilic reactant used in Step (c) | Temperature which may be used in Step (c) |
| --- | --- |
| Chlorine | 0° C. to −5° C. |
| Bromine | −5° C. to ambient temperature |
| Iodine | −5° C. to ambient temperature |
| Water | 0° C. to ambient temperature |
| Hydrogen peroxide | −50° C. to −60° C. |
| Tert-butyl hydroperoxide | −60° C. to ambient temperature |
| Copper chloride | −5° C. to ambient temperature |

The 3-methylene quinuclidine used as starting product in the process according to the invention is a known compound which may be prepared, in particular, by the action of triphenylmethyl-phosphonium bromide on 3-quinuclidinone (Wittig reaction). The process according to the invention therefore permits compounds of formula (I) to be obtained from 3-methylene quinuclidine in only four steps, and without it being necessary to isolate the intermediate products formed.

The following examples illustrate the invention, without limiting it.

EXAMPLE 1

Preparation of 3-chloromethyl quinuclidine (a) To a suspension of 3.8 g (0.1 mole) of lithium aluminum hydride in 50 cm$^3$ of tetrahydrofuran, placed under an atmosphere of nitrogen and maintained at a temperature of 20° C., was added with stirring, a solution of 9.8 g (0.08 mole) of 3-methylene quinuclidine in 30 cm$^3$ of toluene. After stirring the reaction medium for 15 minutes, 0.6 cm$^3$ of titanium tetrachloride were added while keeping the temperature approximately 15° C. The black suspension obtained was then agitated for 24 hours at the ambient temperature. After this period of time, the reaction medium no longer contained any 3-methylene quinuclidine, as was shown by a check carried out using gas chromatography.

(b) The suspension obtained at the end of step (a) above was cooled to −5° C. Then 17 g (0.19 mole) of anhydrous ethyl acetate were added dropwise, while maintaining the temperature below or equal to 5° C., and the suspension was stirred for one hour at the ambient temperature.

(c) The suspension obtained at the end of step (b) above was cooled to −5° C., and then a current of chlorine was bubbled slowly into the reaction medium, while the temperature of the medium was held at less than or equal to 0° C. The reaction medium decolorized progressively. The bubbling of chlorine was stopped when 23 g (0.32 mole) of chlorine had been absorbed.

The reaction medium was then kept under agitation for one hour at 0° C., and then 100 cm$^3$ of an N aqueous solution of hydrochloric acid were added slowly without allowing the temperature to exceed 5° C. After stirring, the aqueous phase was decanted, washed twice, each time with 40 cm$^3$ of toluene, then cooled to 0° C. and made alkaline by the addition of 150 cm$^3$ of a 30% aqueous solution of sodium hydroxide. The product formed was extracted three times, each time with 30 cm$^3$ of toluene. The toluene phases were collected, washed with 15 cm$^3$ of water, dried over sodium sulfate, and 30 cm$^3$ of a solution (about 5N) of hydrochloric acid in isopropanol were added. The crystals obtained were filtered and washed with acetone. In this way, 11.7 g (which corresponds to a yield of 75% calculated on the 3-methylene quinuclidine used) of the hydrochloric of 3-chloromethyl quinuclidine were obtained, which sublimed at 265° C.

EXAMPLE 2

Preparation of 3-bromomethyl quinuclidine (a) The operation was carried out as in step (a) of Example 1, starting with 5.7 g of lithium aluminum hydride in 75 cm$^3$ of tetrahydrofuran, 14.7 g (0.119 mole) of 3-methylene quinuclidine in 45 cm$^3$ of toluene and 0.9 cm$^3$ of titanium tetrachloride.

(b) To the suspension obtained at the end of step (a), were added 30 ml of anhydrous ethyl acetate, while maintaining the temperature of the medium at about 0° C. The reaction medium was then agitated for one hour at the ambient temperature.

(c) The reaction medium obtained at the end of step (b) above was cooled to −5° C., and then 22.2 g (0.139 mole) of bromine were added while keeping the temperature of the medium below or at +5° C. The reaction medium was then agitated for 4 hours at the ambient temperature.

Then, while keeping the temperature of the medium between 10° and 15° C., there were added successively, 5.7 ml water, 4.5 ml of a 20% aqueous solution of sodium hydroxide and 19.8 ml of water. The precipitate obtained was filtered and washed with toluene. The filtrate and the toluene used for washing the precipitate were collected, and a solution of hydrochloric acid in ethanol was added until the pH of the medium reached a value of 1. The medium was then concentrated by distillation under vacuum and the residue taken up in 100 ml of acetone. The crystals obtained were separated by filtration. 19 g (which correspond to a yield of 66.6% calculated on the 3-methylene quinuclidine used) of the hydrochloride of 3-bromomethyl quinuclidine were thus obtained, which melted at 264°–266° C.

EXAMPLE 3

Preparation of 3-iodomethyl quinuclidine (a) The operation was carried out as in step (a) of Example 2.

(b) The operation was carried out as in step (b) of Example 2.

(c) The reaction medium obtained at the end of step (b) was cooled to −5° C., and then 35.5 g (0.14 mole) of iodine in solution in 300 ml of toluene were added, the temperature of the medium being maintained between 0° C. and +5° C. Then the reaction medium was stirred for 4 hours at the ambient temperature.

The reaction medium was then treated as indicated in step (c) of Example 2. 17 g (which corresponds to a yield of 50% calculated on the 3-methylene quinuclidine used) of the hydrochloride of 3-iodomethyl quinuclidine were obtained, which melted at 196°–198° C., with decomposition.

EXAMPLE 4

Preparation of 3-hydroxymethyl quinuclidine (a) The operation was carried out as in step (a) of Example 1, starting from 4.8 g of lithium aluminum hydride in 60 cm$^3$ of tetrahydrofuran, 12.3 g (0.1 mole) of 3-methylene quinuclidine in 40 cm$^3$ of toluene and 0.75 cm$^3$ of titanium tetrachloride.

(b) The operation was carried out as in step (b) of Example 2.

(c) The reaction medium obtained at the end of step (b) was cooled to −60° C. and placed under a current of nitrogen, and 13 g of a 30% aqueous solution of hydrogen peroxide (or 0.115 mole of hydrogen peroxide) was added dropwise, while keeping the temperature of the medium below or at −50° C. The reaction medium was then maintained at −60° C. for one hour.

Then 80 cm$^3$ of soda lye were added to the medium, the temperature of the medium was allowed to increase to about 20° C., and the medium was then extracted four times, each time with 80 cm$^3$ of diethyl oxide. The diethyl oxide phases were collected, dried and the solvent removed by distillation. The residue obtained was taken up in 80 cm$^3$ of petroleum ether. The obtained crystals were separated by filtration and dried under vacuum in the presence of P$_2$O$_5$. 4.5 g (which corresponds to a yield of 32.6% calculated on the 3-methylene quinuclidine used) of 3-hydroxymethyl quinuclidine were obtained, which melted at 59° C.

EXAMPLE 5

Preparation of 3-hydroxymethyl quinuclidine (a) The operation was carried out as in step (a) in Example 1, starting with 48 g of lithium aluminum hydride in 600 cm$^3$ of tetrahydrofuran, 123 g (1 mole) of 3-methylene quinuclidine in 400 cm$^3$ of toluene, and 7.5 cm$^3$ of titanium tetrachloride.

(b) To the suspension obtained at the end of step (a) was added 300 ml of anhydrous ethyl acetate, while keeping the temperature of the medium at about 0° C. After the addition was complete, the reaction medium was agitated for one hour at the ambient temperature.

(c) The medium obtained at the end of step (b) was cooled to about −60° C., and 95 g (1.05 mole) of tert-butyl hydroperoxide were added slowly. The reaction medium was then agitated for 17 hours at the ambient temperature.

Then, while keeping the medium at a temperature of from 0° C. to +10° C. under an atmosphere of nitrogen, were added successively, 32 ml of water, 67 ml of a 30% aqueous solution of sodium hydroxide and finally 85 ml of water. The precipitate obtained was filtered and washed with toluene. The filtrate and the toluene used for washing the precipitate were collected and concentrated by distillation under reduced pressure. The residue was taken up with 300 ml of di-isopropyl ether. The crystals obtained were separated by filtration. 63 g (corresponding to a yield of 45% calculated on the 3-methylene quinuclidine used) of 3-hydroxymethyl quinuclidine were obtained.

EXAMPLE 6

Preparation of 3-methyl quinuclidine (a) The operation was carried out as in step (a) of Example 1, starting with 4.7 g of lithium aluminum hydride in 60 ml of tetrahydrofuran, 12.3 g of 3-methylene quinuclidine in 40 ml of toluene, and 0.7 ml of titanium tetrachloride.

(b) To the suspension obtained at the end of step (a), 25 ml of anhydrous ethyl acetate were added, while maintaining the temperature of the medium at about 0° C., and the suspension was stirred for one hour at the ambient temperature.

(c) The reaction medium obtained at the end of step (b) was cooled to about 0° C. and then under a current of nitrogen, 3.2 ml of water, then 5.5 ml of a 30% aqueous solution of sodium hydroxide and then 8.5 ml of water were added slowly. The reaction medium was then agitated for 30 minutes at the ambient temperature. The white precipitate obtained was filtered and washed with 30 ml of toluene. The filtrate and the toluene used for washing the precipitate were collected and dried over sodium sulfate, and then, while keeping the temperature of the medium between 0° C. and +5° C., a solution of hydrochloric acid in ethanol was added slowly until the pH of the medium reached a value of 1. The medium was then concentrated by distillation under reduced pressure. The residue obtained was taken up in 80 ml of acetone. The crystals formed were separated by filtration. 11.4 g (which corresponds to a yield of 91% calculated on the 3-methylene quinuclidine used) of the hydrochloride of 3-methyl quinuclidine were thus obtained.

EXAMPLE 7

Preparation of 3-chloromethyl quinuclidine (a) The operation was carried out as in step (a) of Example 1, starting with 4.7 g of aluminum lithium hydride in 60 ml of tetrahydrofuran, 12.3 g of 3-methylene quinuclidine (0.1 mole) in 40 cm$^3$ of toluene and 0.7 ml of titanium tetrachloride.

(b) The operation was carried out as in step (b) of Example 6.

(c) The medium obtained at the end of step (b) was cooled to a temperature of from 0° C. to −5° C., and 27 g (0.2 mole) of copper chloride were added slowly while keeping the temperature of the medium below or at +5° C. during the addition.

Then the reaction medium was agitated for one hour at the ambient temperature. While cooling to about 10° C., 15 ml of water and 25 ml of a 37% concentrated aqueous solution of hydrochloric acid were added. The cuprous chloride precipitate formed was separated by filtration and washed with 10 ml of water. The organic phase was removed by decantation and the aqueous phases collected and made alkaline by the addition of a 32% aqueous solution of sodium hydroxide until the pH of the aqueous medium was about 14, the temperature of the medium being maintained at between 10° C. and 20° C. during alkalinization. The aqueous medium was then extracted 3 times, each time with 40 ml of toluene. The collected toluene phases were washed with 20 ml of water, dried over sodium sulfate and 40 cm$^3$ of a 5N solution of hydrochloric acid in isopropanol were added. The crystals formed were filtered and washed with acetone. 12.5 g (which corresponds to a yield of 64% calculated on the 3-methylene quinuclidine used)

of the hydrochloride of 3-chloromethyl quinuclidine were thus obtained.

EXAMPLE 8

Preparation of 3-chloromethyl quinuclidine (a) The operation was carried out as in step (a) of Example 1, starting from 2.28 g of lithium aluminum hydride in 50 ml of tetrahydrofuran, 6.15 g (0.05 mole) of 3-methylene quinuclidine and 0.7 g of zirconium tetrachloride (instead of 0.6 ml of titanium tetrachloride).

(b) The operation was carried out as in step (b) of Example 6.

(c) The operation was carried out as in step (c) of Example 7, using 13.5 g (0.1 mole) of copper chloride instead of 27 g of copper chloride.

The operation was completed as set forth in Example 7. 4.68 g (which corresponds to a yield of 48% calculated on the 3-methylene quinuclidine used) of the hydrochloride of 3-chloromethyl quinuclidine were thus obtained.

EXAMPLE 9

Preparation of 3-methyl quinuclidine (a) To 120 cm³ of tetrahydrofuran, placed under a nitrogen atmosphere and maintained at a temperature of 0° C., were added dropwise 34.6 g (0.12 mole) of bis(2-methoxy ethoxy)aluminum sodium hydride in the form of a solution in toluene. 12.3 g of 3-methylene quinuclidine were then added with stirring, and 0.9 ml of titanium tetrachloride were added while keeping the temperature at 0° C. The temperature of the reaction medium was then allowed to increase to the ambient temperature and the reaction medium was stirred for 48 hours.

(b) The operation was carried out as in step (b) of Example 6.

(c) The operation was carried out as in step (c) of Example 6.

6 g of a mixture of crystals of 3-methyl quinuclidine hydrochloride and 3-methylene quinuclidine hydrochloride were finally obtained.

What is claimed is:

1. Process for the preparation of a compound of the formula:

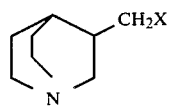
(I)

in which X is chlorine which comprises the steps of:
a. reacting 3-methylene quinuclidine of the formula:

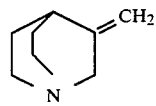
(II)

in an appropriate solvent and in the presence of a catalytic quantity of a halide of a transition metal, with an aluminum hydride, at a molar ratio

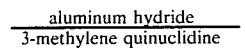

of at least 0.6;

b. reacting the product formed in step a in situ with an ester of a saturated aliphatic alcohol having 1 to 6 carbon atoms and a monocarboxylic saturated aliphatic acid having 1 to 6 carbon atoms; and c. reacting the product formed in step b in situ with an electrophilic reactant capable of yielding an atom of chlorine.

2. Process according to claim 1 wherein the solvent used in step a is tetrahydrofuran, dimethoxyethane, diglyme, triglyme, mixtures of these compounds, or mixtures of these compounds with not more than 50% by volume of an aromatic hydrocarbon.

3. Process according to claim 1 wherein in step a, titanium tetrachloride, zirconium tetrachloride, cobalt chloride or nickel chloride is used as the transition metal halide, and lithium aluminum hydride or bis(2-methoxy ethoxy) aluminum hydride is used as the aluminum hydride.

4. Process according to claim 3, wherein in step a, lithium aluminum hydride is used as the aluminum hydride, titanium tetrachloride is used as the transition metal halide, and the reaction is carried out with a molar ratio

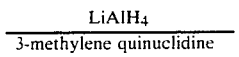

of 1.2 to 1.3, and with a molar ratio

of between 10 and 25.

5. Process according to claim 1 wherein ethyl acetate or methyl formate is used as the ester in step b.

6. Process according to claim 1 wherein the electrophilic reactant in step c is selected from chlorine, copper chloride and N-chlorosuccinimide.

7. Process according to claim 6 for the preparation of 3-chloromethyl quinuclidine wherein the electrophilic reactant in step c is chlorine and wherein step c is carried out at a temperature within the range of 0° C. to −5° C.

8. Process according to claim 6 for the preparation of 3-chloromethyl quinuclidine wherein the electrophilic reactant in step c is copper chloride and wherein step c is carried out at a temperature within the range of from −5° C. to the ambient temperature.

* * * * *